United States Patent
Streelman et al.

(10) Patent No.: US 6,720,150 B2
(45) Date of Patent: Apr. 13, 2004

(54) METHOD FOR IDENTIFYING FAST-GROWING FISH

(75) Inventors: Jeffrey Todd Streelman, Durham, NH (US); Thomas David Kocher, Durham, NH (US)

(73) Assignee: University of New Hampshire, Durham, NH (US)

( * ) Notice: Subject to any disclaimer, the term of this patent is extended or adjusted under 35 U.S.C. 154(b) by 0 days.

(21) Appl. No.: 10/190,163

(22) Filed: Jul. 3, 2002

(65) Prior Publication Data

US 2003/0047143 A1 Mar. 13, 2003

Related U.S. Application Data (60) Provisional application No. 60/315,156, filed on Aug. 27, 2001.

(51) Int. Cl.[7] .............................................. A01K 67/00
(52) U.S. Cl. ............................... 435/6; 800/21; 119/215
(58) Field of Search ........................... 119/215; 800/20, 800/21; 435/6

(56) References Cited

U.S. PATENT DOCUMENTS

| | | | | |
|---|---|---|---|---|
| 5,082,779 A | * | 1/1992 | Rottman et al. | 800/25 |
| 5,122,513 A | * | 6/1992 | Devlin et al. | 514/12 |
| 2003/0047143 A1 | * | 3/2003 | Streelman et al. | 119/215 |

OTHER PUBLICATIONS

Auperin et al. 1996. The role of prolactin in the adaptation of Tilapia to hypo- and hyperosmotic environments. in The third international symposium on Tilapia aquaculture (ed. by Pullin et al.).*

(List continued on next page.)

*Primary Examiner*—Peter M. Poon
*Assistant Examiner*—Jeffrey L. Gellner
(74) *Attorney, Agent, or Firm*—Devine, Millimet & Branch PA; Paul Remus; Kristin Kohler (57) ABSTRACT

Methods of selecting fish for breeding and optimum growth in conditions of various salinity are disclosed. Fish are selected for growth in specific salinity based on their prolactin 1 genotype. A simple sequence repeat polymorphism (microsatellite) in the tilapia prolactin (prl 1) promoter is associated with differences in prl 1 expression and differences in growth in "salt-challenged" or "salt-effected" fishes. This discovery suggests that dinucleotide microsatellites may represent an under-appreciated source of genetic variation for regulatory evolution, and belie the textbook interpretation that non-coding microsatellite length variation lacks functional consequences. Thus, the methods of the invention include determining or selecting the salinity of the environment in which the fish will be grown; determining the prolactin genotype of at least one male and at least one female fish being considered for breeding; breeding male and female fish having the desired genotype(s) to result in offspring having known, predictable genotypes; and raising the fish in a salinity environment compatible with the fishes' genotype(s).

6 Claims, 4 Drawing Sheets

OTHER PUBLICATIONS

Tayamen et al. 2002 (discussed at meeting held 1996). Tilapia brookstock development for saline waters in the Phillines. ICLARM Quarterly 25(1): 32–38.*

Bole–Feysot et al. 1998. Prolactin (PRL) and its receptor: Actions, Signall, transduction pathways and phenotypes observed in PRL receptor knockout mice. Endocrine Reviews 19(3):225–268. p. 226.*

Streelman et al. 2002. Microsatellite variation associated with prolactin expression and growth of salt–challenged tilapia. Physiol. Genomics 9: 1–4.*

Anonymous. Apr.–May 2002. A gene for salinity tolerance in tilapia: microsatellites are directly selected! at www.genecomp.com.*

Alfred Nordheim and Alexander Rich, "The sequence (dC–dA)n* (dG–dT)n forms left–handed Z–DNA . . . ," Proc. Natl.Acad.Sci., p. 1821–1825, ( Apr. 3, 1983).

WJ Lee and TD Kocher, "Microsatellite mapping of the prolactin locus . . . ," Animal Genetics, International Society for Animal Genetics, ( Jul. 3, 1998).

Louise H. Naylor and Elizabeth M. Clark, "d(TG)n*d(CA)n sequences upstream of the rat prolactin gene . . . ," Nucleic Acids Research, Oxford University Press, vol. 18 ( No. 6), ( Jul. 3, 1990).

D. Swennen et al., "Structure of the Tilapia (*Oreochromis mossambicus*) Prolactin I Gene," DNA Cell Biology, vol. 11 ( No. 9), p. 673–684, ( Jul. 3, 1992).

* cited by examiner

METHOD FOR IDENTIFYING FAST - GROWING FISH

RELATED APPLICATIONS

This application claims the benefit of Ser. No. 60/315,156 which was filed on Aug. 27, 2001.

GOVERNMENT SPONSORSHIP

This Invention is funded in part by NSF DBI 9803946, USDA/NRICGP 00352059287.

COPYRIGHT

A portion of the disclosure of this patent document contains material that is subject to copyright protection. The copyright owner has no objection to the facsimile reproduction by anyone of the patent document or the patent disclosure as it appears in the United States Patent and Trademark Office patent file or records, but otherwise reserves all copyright rights whatsoever.

FIELD OF THE INVENTION

The invention relates to selection of fish for optimum growth. More particularly the invention relates to methods of selecting fish, in particular tilapia, for optimum growth in water of differing salinity. Most particularly the invention relates to using a polymorphism in the tilapia prolactin gene to select and then breed fish, based on genotype, for optimum growth in water of differing salinity.

BACKGROUND OF THE INVENTION

Tilapia are among the world's most important aquacultural finfishes and include any of numerous, mostly freshwater, fish species (genus Tilapia, family Cichlidae) native to Africa. Tilapias resemble North American sunfishes and one species can grow to up to 20 lbs (9 kg). Tilapia species are popular as aquacultural fishes because they are easy to raise and harvest for food. They grow rapidly, resist disease, and eat readily abundant algae and zooplankton. As a result, tilapia have been used in warm-water aquaculture systems since the early Egyptian civilization and have been introduced into many freshwater habitats. In addition, some tilapia also grow well in saltwater, and various strains differ in their tolerance to saltwater. For example, in certain areas of the world it is preferable to grow tilapia in bays or brackish waters, but not all individuals grow well in these conditions. In fact, tilapiine species differ greatly in salt tolerance and growth response in different salinities. Thus, it has been, and continues to be somewhat difficult to select or predict which individuals will grow best at which salinity.

A multitude of studies have addressed means to grow bigger tilapia faster. As with any food animal, producers look for ways to select and grow larger animals in less time. Thus the use of growth hormones has been investigated to various extent with most types of food animals, including tilapia. In addition, there have been experiments with water temperature, salinity and hybridization. However, there is no present method, other than trial and error, to identify tilapia strains for growth in different salinities.

With respect to hormones, a great deal is known about the role of peptide hormones in fish osmoregulation. Prolactin is a member of the GH/Prl gene family whose "freshwater adapting" role is to increase plasma osmolality by reducing gill $Na^+K^+ATP$-ase activity. The tilapiine pituitary produces two forms of prolactin, encoded by different genes, prl 1 and prl 2, which differ in both molecular weight (24 and 20 kD respectively) and number of amino acid residues (188 and 177 respectively). These two forms are roughly 70% identical at the amino acid level and appear to have differential osmoregulatory and somatotropic actions. Past experiments suggest that as fishes move into more saline environments, both prolactin mRNA's as well as serum levels of prolactin decrease, and this effect is more dramatic for prolactin 1.

Figure 1:
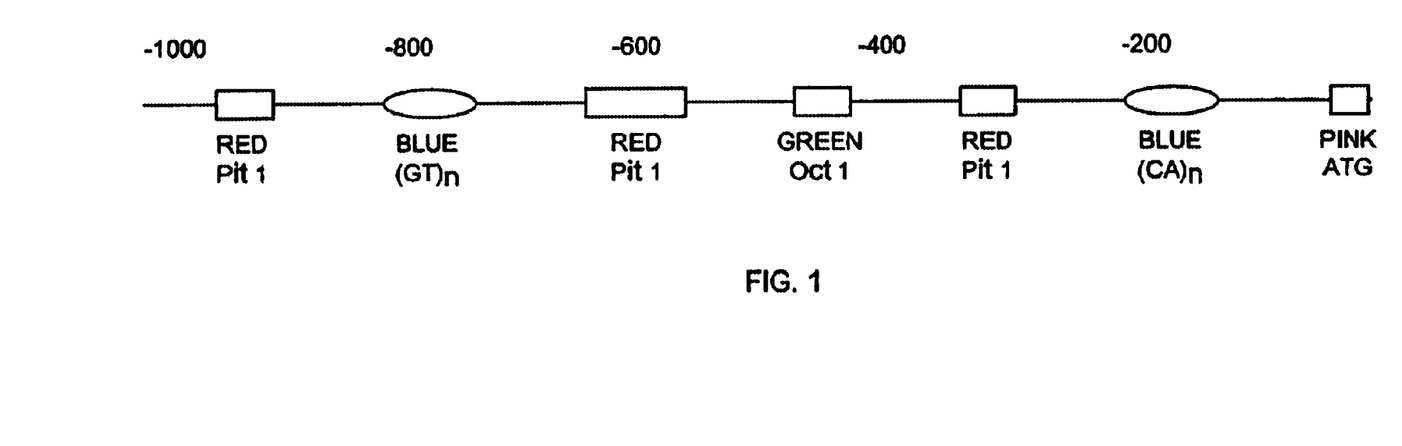
FIG. 1 (Prior Art) is a schematic representation of the tilapia prl 1 promoter region. Identification of putative transcription factor binding sites (e.g. Pit 1) follows the methods of Swennen et al. DNA and Cell Biol. 11a;673–684, 1992.

The tilapia prl 1 promoter shares non-canonical elements with that of the rat. Both promoters have two $(CA)_n$ microsatellites (short sequences of repeated nucleotides) interspersed among putative binding sites for the pituitary-specific transcription factor Pit-1 (See FIG. 1). Naylor and Clark (Naylor L. H. and Clarke E. M. Nucleic Acids Res 18: 159501601, 1990) demonstrated in rat that these repeat sequences formed left-handed Z-DNA in vitro and repressed prl 1 expression. At present, microsatellites and non-coding microsatellite length variation among individuals of a species are generally thought to be neutral and lack functional consequences, except perhaps being related to certain genetic diseases, and have generally not been investigated at length. However, despite the textbook interpretation that non-coding simple sequence repeats evolve in a neutral fashion, recent reports have indicated otherwise. In fact, the abundance and position of dinucleotide microsatellites in eukaryotic genomes, coupled with a high rate of mutation, suggest a potential and pervasive role for microsatellites in gene regulation.

Therefore it would be desirable to have a simple method, based on a variety of genotype, to identify and select animals (for example, tilapia) for optimum growth in differing salinity conditions. Such a method would eliminate the need to experiment with the fishes' growing environment/aquaculture conditions, as well as eliminate the need to supplement the fish with growth stimulants or other artificial means.

SUMMARY OF THE INVENTION

The invention most generally relates to providing a reliable means for selecting and breeding fish for optimum growth in different salinities. In developing the invention, Applicants simply used a natural system to evaluate the association between dinucleotide microsatellite variation, quantitative differences in gene expression and the physiological response to contrasting environments. Applicants' work, in fact, provides the first in vivo evidence that differences in microsatellite length among individuals may indeed affect gene expression and that variance in expression has concomitant physiological consequences.

A most basic embodiment of the invention, therefore, preferably uses differences among individual fish in the length of a simple sequence repeat stretch of DNA (a microsatellite) in the prolactin 1 promoter to select individuals for optimum growth in different salinities. The invention includes methods of selecting individual fish for optimum growth in conditions of various salinity. Fish are selected for breeding and raising in a specific salinity based on their prolactin genotype.

Applicants discovered that a simple sequence repeat polymorphism (microsatellite) in the tilapia prolactin 1 (prl 1) promoter is associated with differences in prl 1 expression and growth in "salt-challenged" or "salt-effected" fishes. This discovery suggests that dinucleotide microsatellites may represent an under-appreciated source of genetic variation for regulatory evolution, and belie the textbook interpretation that non-coding microsatellite length variation lacks functional consequences. In developing the invention, Applicants reasoned that a regulatory effect similar to that found with respect to microsatellite repeat sequences that formed Z-DNA and repressed prl 1 in the rat (Naylor L. H. and Clarke E. M. *Nucleic Acids Res* 18: 1595–1601, 1990) may be found in other species even though microsatellite length variation is generally thought to lack functional consequences. In the present invention Applicants investigated whether any regulatory effect might be present in tilapia with respect to microsatellite length of the prl 1 promoter, and whether individual differences in microsatellite length might affect prl 1 expression in vivo and might contribute to the known variance in salt tolerance and growth of tilapia at different salinities.

In fact, Applicants found that the differences in length of the simple sequence repeat stretch of DNA in the tilapia prolactin promoter do elicit changes in the quantity of prolactin that is produced from the pituitary. This variation in prolactin expression is associated with divergent growth rates of individuals in different salt conditions. Applicants found with tilapia that individual variation in microsatellite length does affect prl 1 expression in vivo and contributes to the known variance in salt tolerance and growth. Knowing the optimal genotype/salinity combinations lead to the methods of the present invention in which much better growth rates and reduced growth time to market size can be achieved with tilapia. In the methods of the invention, the prl 1 genotypes of fish are determined, then fish of a desired genotype are selected and bred for optimum growth with respect to genotype for growth in a specific salinity. Once fish of the desired genotype are found and selected they may be bred to result in offspring all having the desired genotype (s) that grows best in the salinity of the aquaculture environment in which the fish will be raised.

Thus the invention provides a simple and inexpensive means to select individuals, based upon their prolactin genotype, for rapid growth in different salinities.

The invention also makes use of a genetic link between a polymorphism in the tilapia prolactin gene and the growth rate of fingerlings at different salinities, from freshwater to full seawater, to select appropriate individuals for breeding and optimal growth at various salinities.

The invention also provides a means to achieve greatly increased growth of individuals selected and grown in the optimal salinity for each individual's genotype. In fact, optimal selection, based on a combination of an individual's prolactin genotype and salinity can result in a two-fold difference in growth rate if the individual is grown in water with a salinity appropriate to its genotype vs. a salinity not compatible with the genotype of the individual.

In addition, the invention also provides a method of selecting fish for breeding such that all offspring are of a prl 1 genotype most compatible with a given or selected (either locally available, or selected, constructed and maintained by the aqua farmer) salinity environment.

DETAILED DESCRIPTION OF THE INVENTION

A most basic embodiment of the invention is a means by which animals, preferably the fish tilapia, can be sorted based on their prolactin genotype, and then bred and raised in an environment with a salinity compatible with their prolactin genotype in order to result in optimum growth.

As noted, past experiments suggest that as fishes move into more saline environments, both prolactin 1 and 2 mRNA's as well as serum levels of prolactin decrease, and this effect is more dramatic for prolactin 1. Thus, Applicants' experiments and examples refer to the prolactin 1 gene, however, the methods of the invention are not limited only to prolactin 1.

In developing the invention Applicants initially concentrated on the microsatellite closest to the start of prl 1 transcription (–200 base pairs, bp). Applicants crossed females of *Oreochromis mossambicus* (salt-adapted) fish with an *Oreochromis niloticus* (freshwater adapted) male carrying microsatellite alleles that differed by 17 repeat units ($CA_{31}$ vs. $CA_{14}$). The *O. mossambicus* dams were homozygous for long alleles ($CA_{31}$) and the *O. niloticus* sire was a heterozygote for long and short alleles. See FIG. 1 for a schematic representation of the tilapia prl 1 promoter region. The $CA_n$ at –200 bp is the region discussed in the examples.

$F_1$ individuals were selected for breeding such that there were three genotypes to follow in the $F_2$ generation: homozygotes for short alleles (hereafter "SS"), homozygotes for long alleles ("LL"), and heterozygotes ("SL"). 75 $F_2$ fishes from the same brood were raised in three salinity treatments in separate 200 L tanks ranging from freshwater (~0 parts per thousand NaCl, "ppt") to 16 ppt to seawater (32 ppt). Two week old fry were acclimated to treatments over a period of 3 days and maintained until fish mass averaged 15 g, (approximately 6 months). Within salt treatments all 3 genotypes were grown in the same tank. At the end of the experimental period fishes were sacrificed, sexed and weighed.

Pituitaries were harvested and stored at –20 degrees C. in RNAlater (Ambion) until RNA extraction. Prl 1 expression was measured from $F_2$ individuals' pituitaries (cDNA preparations) using Taqman probes (PE Biosystems) for real-time PCR with b-actin as a reference. Primers and probes were designed for each cDNA using Primer Express, (version 1.5 Applied Biosystems). Probe binding sites were located at intron-exon boundaries to prevent amplification of genomic DNA. Probes were fluorescently labeled at the 3' end. Fluorescence was monitored during 40 cycles of PCR on a GeneAmp 5700 Sequence Detection System (Applied Biosystems) at 95 degrees C. for 15 seconds, 55 degrees C. for 30 seconds and 65 degrees C. for 1 minute.

Critical cycle number was determined when fluorescence exceeded a threshold value set close to the background. Prl 1 relative gene expression was determined according to the formula $2^{B-actinCT-Prl\ 1\ CT}$ where CT is the critical cycle number. Real-time PCR primer and probe sequences are as follows: F primer, cccatcaacgaactgttcga (SEQ. ID. NO. 1); R primer, gcatgatcaccctgcctatagg (SEQ. ID. NO.2); probe, ctcacccaggagctggactctcacttccctc (SEQ. ID. NO. 3).

$F_2$ individuals were genotyped as described by Lee W. J, and Kocher T. D. in *Microsatellite Mapping of the Prolactin Locus in the Tilapia Genome Anim. Genet.* 29: 68–69, 1998 which is incorporated herein by reference in its entirety, or by a Sac II RFLP in prl 1 cDNA that distinguishes parental alleles. Those of skill in the art would know the Sac II method. Differences among genotypes and treatments were evaluated by one-way ANOVA and appropriate post hoc multiple comparison tests.

Results

Figure 2A:
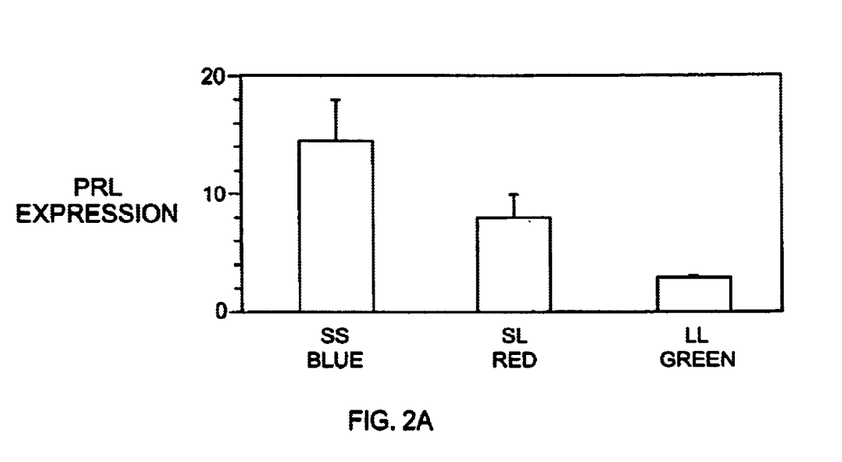
FIGS. 2a–f illustrate the effects of differing prl 1 expression and fish mass across different salt water treatments.

Females were larger than males across all salinity treatments but did not differ from males in prl 1 expression. In general, mean fish mass increased with increasing salinity ($p=8.4\times10^{-06}$). Expression differed among genotypes at 0 ppt (p=0.006); SS individuals expressed approximately 2 times as much prl 1 as SL fishes and approximately 7 times as much prl 1 as LL fishes. These results are shown in FIG. 2a. All graphical representations shown in FIGS. 2a–f depict means+/–standard errors.

Figure 2B:
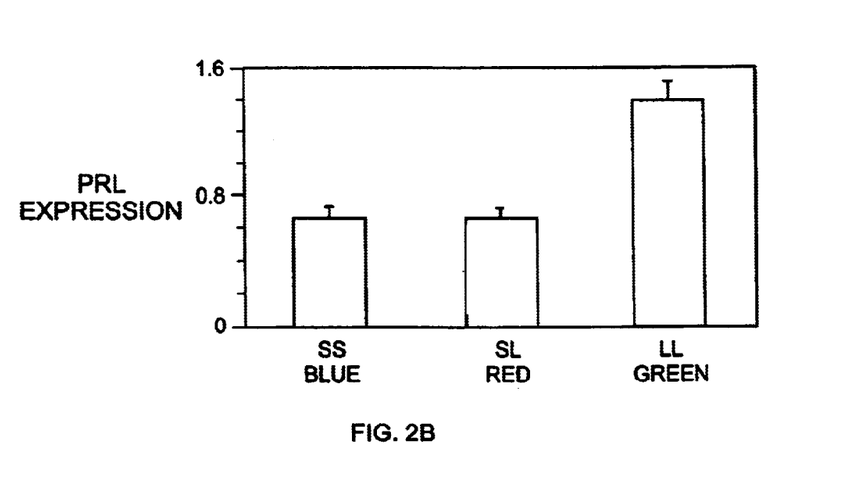
Figure 2C:
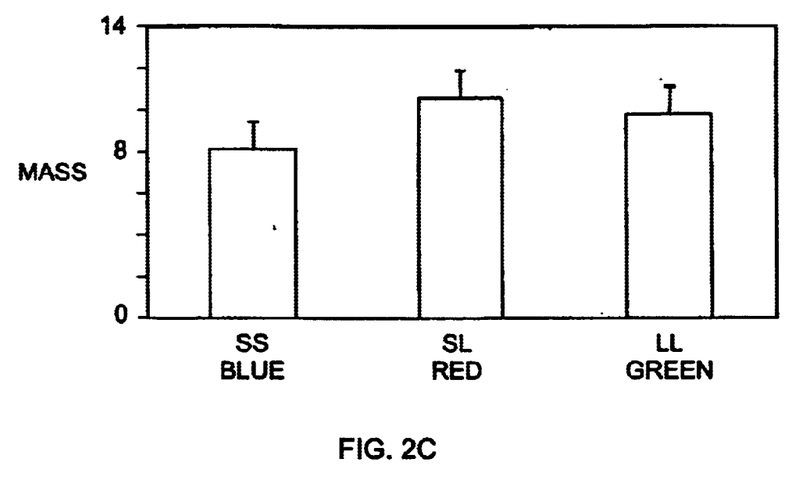
Figure 2D:
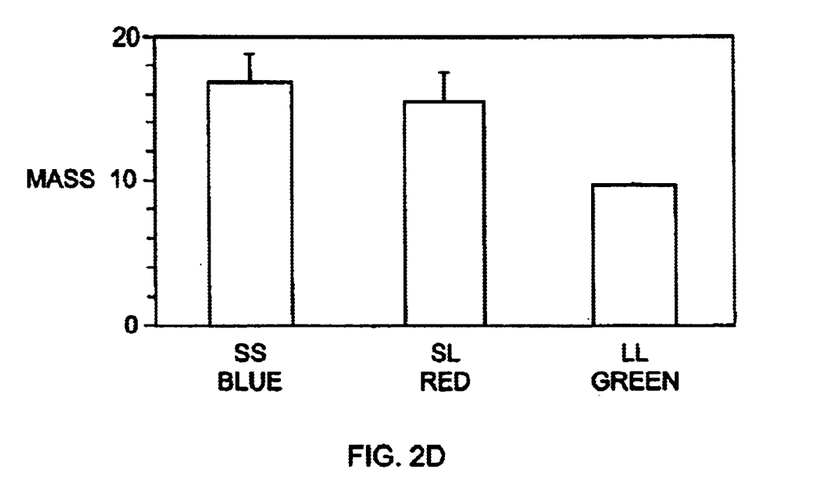

Expression differed among genotypes at 16 ppt (p=0.0005) but with a near-opposite pattern to that seen in freshwater. Individuals of genotype LL expressed twice as much prl 1 as did fishes of genotypes SS and SL, as shown in FIG. 2b. Notably, however, LL individuals were nearly twice as small as those of other genotypes at 16 ppt, as shown in FIG. 2d, whereas the SS individuals were the smallest at 0 ppt as shown in FIG. 2c. However, there were no differences among the three genotypes in either prl 1 expression or fish mass at 32 ppt. All genotypes grew fairly well at 32 ppt and these data are not shown, but see FIG. 2f for the masses of the three genotypes at 32 ppt.

Figure 2E:
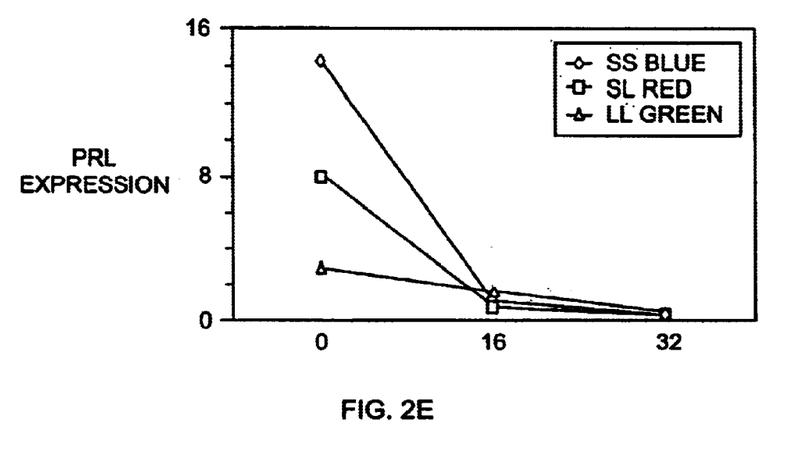

There were significant genotype×environmental interactions detected for all genotypes. For all genotypes, both prl 1 expression and mass differed across salt treatments. For SS: $p=1.5\times10^{-05}$ for expression and p=0.03 for mass. For SL: $p=3.8\times10^{-06}$ for expression and p=0.008 for mass. For LL: p=0.0008 for expression and p=0.06 for mass. Individuals of genotype SS and SL showed dramatic decreases (greater than 10-fold) in prl 1 expression from 0–16 ppt. This response was not nearly as apparent for genotype LL, as shown in FIG. 2e.

Figure 2F:
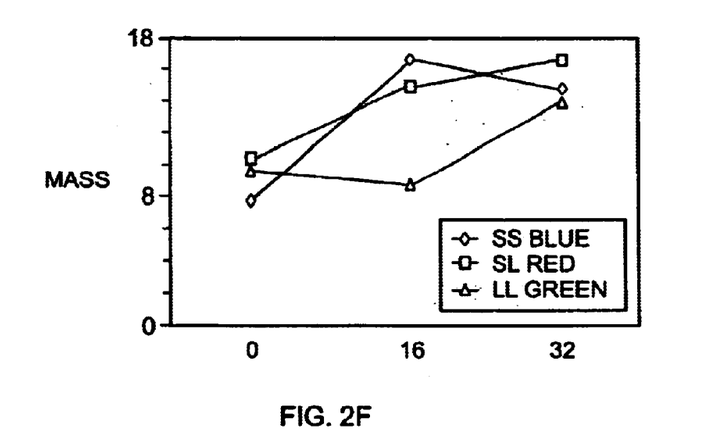

Each genotype grew best at a different salinity as shown in FIG. 2f, and mean growth of genotypes was inversely correlated with mean prl 1 expression across salinities. For SS: $r^2=0.957$, for SL: $r^2=0.971$, and for LL: $r^2=0.530$. However, FIGS. 2e and 2f demonstrate divergent norms of reaction for each genotype in response to external salt concentration. In natural populations these "crossover interactions" are prima facie evidence for the adaptive maintenance of genetic variation in the fluctuating environments. In other words, while there are conditions under which some genotypes thrive better than others, all three genotypes are able to grow in salinity conditions ranging from freshwater to seawater. The variety of the genotypes thus allows adaptation to various environments using the same gene. This correlates with Applicants' initial investigation into the supposedly non-functional variation in microsatellites that may indeed have a very important function.

The possibility that runs of alternating purines and pyrimidines might affect gene expression was suggested nearly 20 years ago by Alexander Rich and others (Nordheim, A. and Rich, A., *Proc. Natl. Acad. Sci. USA* 80: 1821–1825, 1983). This suggestion, and Applicants' surprising results suggest that repeats of varying length can induce promoter conformations that differ in their ability to bind transcriptional regulators. There is good evidence that tilapia prl 1 expression is regulated in response to plasma osmolality, perhaps via interactions with Pit-1. Long prl 1 microsatellite alleles may thus act as insulators, restricting access of enhancers (for example, freshwater) and repressors (for example, saltwater) to Pit-1 sites.

Because $F_2$ fishes are not isogenic lines segregating for different microsatellite alleles, one can not formally exclude the possibility that the alleles followed by Applicants are in linkage disequilibrium with an unmeasured, causal polymorphism. However sequence from 1.2 Kb of the prl 1 promoter in SS vs. LL individuals revealed no consistent substitutions in known regulatory element binding sites. In fact, additional sequence differences in this region are found in the second simple sequence repeat 800 bp upstream of the start codon. Individuals of genotype SS had shorter alleles ($GT_{14}$) than LL fishes ($GT_{39}$) at this repeat.

Taken together, both microsatellites in the prl 1 promoter of SS fishes are less than half the size of the corresponding sequence in LL individuals. These results show a pattern of positive covariance contrasting with data from other bony fishes. It is possible that these simple sequence repeats interact with one another to elicit transcriptional change.

Although others have suggested the possibility of a functional role for microsatellites, Applicants' results provide the first in vivo evidence that differences in microsatellite length among individuals may affect gene expression and that variance in expression has concomitant physiological consequences. These results run counter to the textbook interpretation that dinucleotide microsatellite variation lacks functional consequences.

The negative correlation between prl 1 expression and fish mass is more difficult to explain. Both prolactin and growth hormone are activated by Pit-1 in distinct pituitary cell lineages and these hormones have antagonistic affects on fish osmoregulation. Applicants' data do not discern whether growth effects are mediated via osmoregulatory differences or transcriptional inhibition of GH-expressing somatotrophs.

From an evolutionary perspective, as noted above, Applicants' results run counter to the textbook interpretation that dinucleotide microsatellite variation lacks functional consequences. These loci are rapidly evolving and ubiquitous components of eukaryotic genomes. Found preferentially in non-coding DNA, dinucleotide repeats provide a means to alter the amount of gene product among individuals without changing the amino acid sequence of the protein or peptide. The association of microsatellites with a long list of transcription factors and environmentally regulated genes suggests an under-appreciated role for microsatellites in the fine-scale modulation of gene expression. Although Applicants have not determined the exact mechanism by which salinity toleration in tilapia is regulated, the link Applicants have discovered between the microsatellite variations and salinity toleration have enabled Applicants to develop a simple and inexpensive means to select individual fish, based on their prolactin genotype, for rapid growth in different salinities.

Thus, the method of the invention includes determining or selecting the salinity of the environment in which the fish will be grown, determining the prolactin (prl 1) genotype of at least one male and at least one female fish being considered for breeding; breeding at least one male and one female fish having the desired genotype(s) to result in offspring having known, predictable genotypes; and raising the offspring in an environment having the selected salinity.

For example, if fresh water were more readily available, cheaper to acquire and maintain a freshwater environment, etc., fish that grow best in fresh water would be desired, (i.e. SL or LL fish) and selected for breeding. Whereas if brackish water (in the range of about 8 ppt to about 16 ppt) were the locally available water supply or were more readily available or desirable SS or SL fish would be the genotypes of choice.

Genotyping the fish is done according to Lee and Kocher (1998), which has been incorporated herein by reference in its entirety, or by a Sac II RFLP in prl 1 cDNA, as noted above. Briefly, the DNA from fishes being typed is extracted from fin clips (a piece of tissue from a fish's fin) in a procedure similar to DNA testing of human hair, for example.

Prolactin 1 microsatellite alleles are amplified by PCR and visualized on acrylamide gels, a type of procedure with which one of ordinary skill in the art would be familiar. The primers and probe used for the genotyping test are as described above, in SEQ. ID. NO.'s 1–3. See also Lee and Kocher 1998.

Once suitable breeding fish have been found, they may be used as stock for establishing a uniform population of fish, all of which have the selectively bred, desired genotypes and are best suited for optimum, maximum growth in the selected salinity.

In addition, the method provides an inexpensive way to establish a fish population best suited to the salinity conditions of the particular growing environment because the genotype testing step need only be done once for each population—to initially find suitable fish for breeding. Once the appropriate fish are selected and are bred, all the offspring will have the desired genotypes and will thrive in the selected salinity. In addition, because all the offspring will be of known genotypes, any of those offspring may then be selected and used for breeding to start new populations of fish having a known genotype, without having to test for the genotype of each fish used for new breeding stock.

While the above description and examples disclose some preferred embodiments of the invention, for example tilapia and prolactin 1, the invention is not limited in scope by the specific embodiments described. The described embodiments are intended as single illustrations of individual aspects of the invention, and functionally equivalent methods and components are within the scope of the invention. For example, the methods of the invention may be adapted for use with other species of fish, and would be particularly useful with other fish bred for food, such as salmon or sea bream. The methods and principles of the invention can also be applied with respect to other genes, such as perhaps prolactin 2. Thus, there may be variations and modifications of the invention, in addition to those shown and described herein, that, while not specifically described, do not depart from the spirit and scope of the invention as described above and in the appended claims, and which will become apparent to those skilled in the art from the foregoing description and accompanying drawings. Such modifications are intended to fall within the scope of the appended claims.

What is claimed is:

1. A method for breeding and raising fish of maximum size comprising:

determining, via a nucleic acid test, a prolactin I genotype of at least one male fish and at least one female fish;

breeding at least one male fish and at least one female fish each having a selected prolactin I genotype, resulting in offspring having selected prolactin I genotypes; and raising said offspring in a salinity environment compatible with maximum growth for the prolactin ii genotype of said offspring, wherein said fish are tilapia.

2. The method of claim 1 wherein said prolactin I genotype is chosen from the group consisting of: homozygous for short allele, homozygous for long allele, and heterozygous for short and long allele.

3. The method of claim 2 wherein said prolactin I genotype most compatible with fresh water is homozygous for long allele or heterozygous for short and long allele.

4. The method of claim 2 wherein said prolactin I genotype most compatible with brackish water is homozygous for short allele of heterozygous for short and long allele.

5. The method of claim 1 wherein said prolactin I genotype of said at least one male fish and said at least one female fish is determined by extracting DNA via at least one fin clip from each fish, amplifying said DNA and visualizing the amplified DNA to determine the prolactin I genotype.

6. A method for establishing a fish population of known genotypes comprising:

determining a prolactin I genotype of at least one male and at least one female fish via a nucleic acid test;

selecting male and female fish for breeding based on their prolactin I genotype;

breeding male and female fish having said selected prolactin I genotypes, to result in off spring having known prolactin genotypes, wherein said fish is tilapia.

* * * * *

SEQUENCE LISTING

```
<160> NUMBER OF SEQ ID NOS: 3

<210> SEQ ID NO 1
<211> LENGTH: 22
<212> TYPE: DNA
<213> ORGANISM: tilapia

<400> SEQUENCE: 1
gcatgatcac cctgcctata gg                                          22

<210> SEQ ID NO 2
<211> LENGTH: 21
<212> TYPE: DNA
<213> ORGANISM: tilapia

<400> SEQUENCE: 2
cccatacaac gaactgttcg a                                           21

<210> SEQ ID NO 3
<211> LENGTH: 31
<212> TYPE: DNA
<213> ORGANISM: tilapia

<400> SEQUENCE: 3
ctcacccagg agctggactc tcacttccct c                                31
```